United States Patent [19]

Shiozaki et al.

[11] 4,366,093

[45] Dec. 28, 1982

[54] CYLINDRICAL MOLDED CATALYST

[75] Inventors: Ken Shiozaki, Hyogo; Kazunori Tsuge, Takasago; Akira Ohnishi, Kakogawa, all of Japan

[73] Assignee: Kanegafuchi Kagaku Kogyo Kabushiki Kaisha, Osaka, Japan

[21] Appl. No.: 249,507

[22] Filed: Mar. 31, 1981

[30] Foreign Application Priority Data

Apr. 7, 1980 [JP] Japan .................. 55-45925

[51] Int. Cl.³ ............................................. B01J 35/02
[52] U.S. Cl. .................................. 252/477 R; 252/463
[58] Field of Search ........................... 252/463, 477 R

[56] References Cited

U.S. PATENT DOCUMENTS 2,408,164  9/1946  Foster ..................... 252/477 R
3,893,952  7/1975  Ryška et al. ............. 252/477 R
4,036,783  7/1977  Blechschmitt et al. ..... 252/461

FOREIGN PATENT DOCUMENTS 51-32492  3/1976  Japan .
54-20475  7/1979  Japan .

Primary Examiner—W. J. Shine
Attorney, Agent, or Firm—Armstrong, Nikaido, Marmelstein & Kubovcik

[57] ABSTRACT

A cylindrical molded catalyst suitable for use in fixed bed reaction having a particular size of 3 to 6 mm. in outer diameter of the circle, at least 1.0 mm. in inner diameter of the circle, at most 1.5 mm. in wall thickness and 3 to 6 mm. in height. The molded catalyst has small resistance to fluid, large effective surface area, good heat conductivity and sufficient mechanical strength, and can produce excellent conversion and selectivity.

3 Claims, No Drawings

CYLINDRICAL MOLDED CATALYST

BACKGROUND OF THE INVENTION

The present invention relates to a novel molded catalyst, and more particularly to a cylindrical molded catalyst.

In order to effectively utilize a catalyst in a fixed catalyst bed, it is desirable that (1) the resistance of a catalyst, i.e. the pressure loss of a fluid caused by the catalyst, is small, (2) the effective surface area of a catalyst is large, and (3) the heat conductivity between catalyst particles or between a catalyst and an inert diluent is good. The shapes of catalysts generally used hitherto are sphere, column and the like. However, in a gas reaction using catalysts of these known shapes, the diffusion of a reactant gas into catalyst particles and the diffusion of a product from the particles are often restricted. That is to say, since in a reaction of a heterogeneous system the reaction is easy to occur selectively in the vicinity of the outer surface of a catalyst, the spherical and columnar catalysts are not efficiently utilized in a reaction. Therefore, in order to attain a desired conversion, it is necessary to use large quantities of a catalyst, and for this purpose, a catalyst packed bed must be lengthened. Further, in case of a columnar catalyst, the pressure loss of a fluid is large, because the void of a catalyst packed bed is small. Also, in case of a spherical catalyst, the heat conductivity is insufficient, because the contact area between catalyst particles is small. In particular, in a reaction accompanying large heat generation such as oxidative reaction, halogenation reaction or hydrogenation reaction, a good heat conductivity is required and, therefore, the use of a catalyst insufficient in heat conductivity may often impair the selectivity of a reaction.

It is an object of the present invention to provide a novel molded catalyst suitable for use in fixed bed reaction.

A further object of the invention is to provide a catalyst having particular shape and size.

A still further object of the invention is to provide a catalyst satisfying the above-mentioned three conditions required for fixed bed use.

These and other objects of the present invention will become apparent from the description hereinafter.

SUMMARY OF THE INVENTION

It has now been found that only a cylindrical catalyst molded in a particular size can satisfy the above-mentioned three conditions required for fixed bed use.

In accordance with the present invention, there is provided a molded catalyst having a cylindrical shape, the outer diameter of the circle being from 3 to 6 mm., the inner diameter of the circle being at least 1.0 mm., the thickness of the wall being at most 1.5 mm. and the height being from 3 to 6 mm.

DETAILED DESCRIPTION

It is necessary that the cylindrical molded catalyst of the present invention has a size of 3 to 6 mm. in outer diameter of the circle, at least 1.0 mm. in inner diameter of the circle, at most 1.5 mm. in thickness of the wall and 3 to 6 mm. in height. The cylindrical catalyst particles of the invention may contain a small portion of catalyst particles having a size outside the above ranges. The preferable catalyst of the present invention is those having an outer diameter of 4 to 5 mm., an inner diameter of 1.5 to 2.5 mm., a wall thickness of 1.0 to 1.5 mm. and a height of 3 to 6 mm.

Although cylindrical catalysts are proposed, these catalysts are all thick in the wall and large in the outer diameter, and no cylindrical molded catalyst having a specific size as defined above has been prepared and put to practical use. The reason would be that it has been considered that a cylindrical catalyst not having a thick wall and a large diameter is insufficient in mechanical strength.

The cylindrical molded catalyst having the specific shape and size of the present invention not only satisfies the before-mentioned three requirements of fixed bed catalyst, i.e. (1) small pressure loss of a fluid, (2) large effective surface area and (3) good heat conductivity between catalyst particles or between catalyst and inert diluent, but also has a mechanical strength sufficient for practical use. Even if the mechanical strength is small to some extent at the time of the preparation of the catalyst, the catalyst can be sufficiently put to practical use without any problem, when the compressive breaking strength of the catalyst in the direction of the diameter of the circle is at least 0.2 kg. In fact, in case of practically using the catalyst of the invention in a reaction, surprisingly the powdering is less than that of a spherical or columnar catalyst.

The catalyst having the specific shape and size of the present invention can be easily produced by a known method such as a compression tabletting method or an extrusion molding method. The mechanical strength of tubular moldings prepared by extrusion molding is samller and of less uniformity than that of moldings prepared by compression molding. Also, moldings having a desired size are easy to obtain by compression molding than extrusion molding. Therefore, a tabletting method using a compression type tabletting machine is preferable, since a better cylindrical molded catalyst can be obtained, which is at least superior in the uniformity of the shape, mechanical strength and density of the moldings. The cylindrical catalyst molded by using a compression type tabletting machine has the further advantages that a catalyst bed is uniformly packed with a catalyst, and as a result, the gas flow becomes uniform and partial deterioration of the catalyst and increase of the pressure loss are hard to occur, since the shape and size of respective tablets are constant. The production of the cylindrical tablets by a compression type tabletting machine can be easily conducted in almost the same manner as the preparation of a usual solid columnar tablet by using a compression molding machine equipped with a mold having a center pestle corresponding to the inner diameter of the circle of the cylindrical catalyst to be prepared. The outer diameter of the cylindrical molded catalyst of the invention is not always required to be constant, and for instance, the cylindrical catalyst may be slightly tapered.

Any catalyst materials used in the preparation of catalysts for heterogeneous reactions are usable in the present invention. Particularly, a mixed material of a carrier material such as alumina, silica or a mixture thereof, and a catalytically effective metal salt or metal oxide is preferable as a material for preparing the cylindrical catalyst of the invention. Particularly useful catalysts molded into the specific cylindrical shape according to the present invention are a catalyst for oxychlorination containing copper halide, a catalyst for chlorination containing iron halide or copper halide and a catalyst for oxidation containing an oxide such as chromium oxide-cobalt oxide, copper oxide or molybdenum oxide. The material for the production of the cylindrical catalyst may contain usual additives such as a binder and a lubricant. The preparation, molding and treatment procedures are conducted in a usual manner. For instance, a mixture of a catalytically effective component and other components such as a carrier may be prepared and molded into the particular cylindrical shape, or after molding a carrier powder into the particular cylindrical shape, a catalytically effective component may be supported on the molding by impregnation.

The cylindrical molded catalyst of the present invention has the advantages that the weight of the catalyst necessary for filling a prescribed volume of a reactor is reduced, thus bringing about the cost reduction, that the outer surface area of the catalyst per unit volume of a reactor is largely increased as compared with a spherical, columnar or crushed shape catalyst and, therefore, the catalytic activity can be increased particularly in a reaction in which the diffusion into pores is the rate-determining step, and in addition to the increase of the activity, undesirable side reactions resulting from insufficient diffusion into pores can be decreased, and that the resistance of the catalyst against a fluid, i.e. the pressure loss, can be decreased.

The smaller the wall thickness of the cylindrical molded catalyst and also the larger the volume of the cylindrical hollow portion, the larger the above-mentioned effects. The lower limit of the wall thickness varies depending on a powder used as a raw material and a binder, and is determined according to a desired mechanical strength of the obtained molded catalyst. An adequate thickness durable for practical use is selected from the range of not more than 1.5 mm. depending on a raw material and binder used. Also, as the ratio of the height to the outer diameter (hereinafter referred to as "H/D") approaches 1, the larger the above-mentioned effects. When the H/D value is more than 2, the pressure loss is decreased, but the heat conductivity becomes bad and the hot spot temperature at the time of reaction becomes too high. Also, when the outer diameter exceeds 6 mm., the catalytic activity, selectivity and heat conductivity are not sufficient, and when the outer diameter is less than 3 mm., the pressure loss becomes large and also the molding cost increases. In the cylindrical molded catalyst having a specified size of the present invention, the H/D value falls within the range of 0.5 to 2. Also, the cylindrical catalyst of a preferable size has the H/D value of 6.0 to 1.5.

In a practical use of the cylindrical molded catalysts of the present invention, it is preferable that the sizes of the cylindrical catalysts packed at the same portion of a reactor in the same operation are of uniformity. Also, though it is preferable that the sizes of the whole cylindrical catalyst particles used fall within the range of the size in the present invention, the cylindrical catalysts packed in a reactor may contain catalysts having a size outside the range of the present invention or catalysts having other shapes so far as the effects of the present invention can be attained.

The present invention is more particularly described and explained by means of the following Examples and Comparative Examples, in which all % are by mole unless otherwise noted.

Although the cylindrical molded catalyst of the present invention is illustrated with reference to an instance of the production of 1,2-dichloroethane by oxychlorination of ethylene in Examples, it is to be understood that the catalyst of the present invention is not limited to such a use and can be used in various reactions in fixed bed to bring about the same effects.

EXAMPLES 1 TO 4 AND COMPARATIVE EXAMPLES 1 TO 7

Magnesium stearate as a lubricant was added to activated alumina powder, and the mixture was molded into tablets having a shape and size as shown in the following Table by employing a compression type tabletting machine. The moldings were then sintered at 500° C. for 3 hours. The molding condition was adjusted so that the sintered moldings had an apparent specific gravity of 1.3 g./cm$^3$. Cupric chloride and potassium chloride were impregnated in the sintered moldings in a usual impregnation manner to provide catalysts supporting 18% by weight of cupric chloride and 1.5% by weight of potassium chloride.

As a reactor, there was used a vertical reactor having a nickel tube of 26.3 mm. in inner diameter and 1,200 mm. in length, a steel pipe of 2 inches in outer diameter connected to an upper portion of the nickel tube, a jacket welded to whole outer surface of the nickel tube and in which a liquid heat medium (registered trademark "Dowtherm" made by Dow Chemical Co.) was circulated, a nickel pipe for temperature measurement of 7 mm. in outer diameter inserted into the central portion of the nickel tube and pressure gauges attached to the inlet and outlet of the the nickel tube for measuring the flow resistance in catalyst bed.

The catalyst was mixed with a spherical fused alumina having a diameter of 5 to 6 mm. to dilute in a concentration of 50% by volume, and 205 ml. of the thus diluted catalyst was packed in the upper half of the reactor. Also, 205 ml. of the nondiluted catalyst was packed in the lower half of the reactor. The reaction was carried out by introducing a reactant gas from the top of the reactor and taking out the reaction gas from the bottom of the reactor. As a reactant gas, 40 N l/hour of hydrogen chloride, 21.6 N l/hour of ethylene and 57 N l/hour of air were supplied to the reactor, and the pressure at the outlet of the reactor was kept at ordinary pressure. The reaction temperature was controlled so that the conversion of the hydrogen chloride fed was maintained 99%. The reaction gas taken out was cooled in two stages first to 5° C. and then to −35° C., and the condensed reaction product and the uncondensed reaction gas were analyzed by gas chromatography in a usual manner.

The results are shown in the following Table, in which the selectivity is based on ethylene.

From the Table, it is observed that the molded catalysts of the present invention are superior in activity, selectivity, pressure loss and heat conductivity to the molded catalysts of Comparative Examples, and also that there is no problem in the increase of the pressure loss by continued reaction.

|   | Ex. 1 | Ex. 2 | Ex. 3 | Ex. 4 | Com. Ex. 1 | Com. Ex. 2 | Com. Ex. 3 | Com. Ex. 4 | Com. Ex. 5 | Com. Ex. 6 | Com. Ex. 7 |
|---|---|---|---|---|---|---|---|---|---|---|---|
| Shape of catalyst | Cylin- | Cylin- | Cylin- | Cylin- | Column | Cylin- | Cylin- | Cylin- | Cylin- | Cylin- | Cylin- |

-continued

|  | Ex. 1 | Ex. 2 | Ex. 3 | Ex. 4 | Com. Ex. 1 | Com. Ex. 2 | Com. Ex. 3 | Com. Ex. 4 | Com. Ex. 5 | Com. Ex. 6 | Com. Ex. 7 |
| --- | --- | --- | --- | --- | --- | --- | --- | --- | --- | --- | --- |
|  | der | der | der | der |  | der | der | der | der | der | der |
| Size of catalyst (mm.) |  |  |  |  |  |  |  |  |  |  |  |
| Outer diameter | 5 | 4 | 4 | 4.6 | 5 | 5 | 4 | 5 | 4 | 6.5 | 2.6 |
| Inner diameter | 2.2 | 1.8 | 1.8 | 2.2 | — | 1.2 | 1.8 | 2.2 | 0.8 | 2.5 | 1.0 |
| Height | 5 | 5 | 3 | 4.6 | 5 | 5 | 10 | 2 | 4 | 6.5 | 5 |
| Wall thickness | 1.4 | 1.1 | 1.1 | 1.2 | — | 1.9 | 1.1 | 1.4 | 1.6 | 2.0 | 0.8 |
| Temperature (°C.) |  |  |  |  |  |  |  |  |  |  |  |
| Heat medium ($T_1$) | 200 | 198 | 197 | 196 | 210 | 207 | 201 | 188 | 202 | 205 | 190 |
| Hot spot ($T_2$) | 285 | 279 | 277 | 274 | 298 | 294 | 296 | 296 | 291 | 303 | 282 |
| $T_2 - T_1$ | 85 | 81 | 80 | 78 | 88 | 87 | 95 | 108 | 89 | 98 | 92 |
| Conversion of HCl (%) | 99.1 | 98.9 | 99.0 | 98.9 | 98.8 | 99.0 | 99.2 | 99.2 | 99.0 | 98.8 | 99.1 |
| Selectivity (%) |  |  |  |  |  |  |  |  |  |  |  |
| 1,2-Dichloroethane | 97.8 | 98.4 | 98.5 | 98.6 | 96.0 | 96.6 | 96.9 | 98.0 | 97.0 | 96.3 | 98.5 |
| Ethyl chloride | 0.3 | 0.2 | 0.2 | 0.2 | 0.7 | 0.5 | 0.5 | 0.3 | 0.5 | 0.7 | 0.3 |
| Other halides | 0.9 | 0.7 | 0.7 | 0.5 | 1.5 | 1.4 | 1.2 | 0.8 | 1.4 | 1.3 | 0.6 |
| Combustion rate of ethylene (%) | 1.0 | 0.7 | 0.6 | 0.7 | 1.8 | 1.5 | 1.4 | 0.9 | 1.1 | 1.7 | 0.6 |
| Pressure loss (mmH$_2$O) |  |  |  |  |  |  |  |  |  |  |  |
| Initial stage of reaction | 5.3 | 5.6 | 6.0 | 5.8 | 9.6 | 7.1 | 4.2 | 10.2 | 8.7 | 3.4 | 18.3 |
| After 500 hours | 5.5 | 5.7 | 6.2 | 6.0 | 12.5 | 7.8 | 4.5 | 15.6 | 9.0 | 3.5 | 19.7 |

What we claim is:

1. A molded catalyst having a cylindrical shape, the outer diameter of the circle being from 3 to 6 mm., the inner diameter of the circle being at least 1.0 mm., the thickness of the wall being at most 1.5 mm. and the height being from 3 to 6 mm.

2. The molded catalyst of claim 1, wherein the outer diameter is from 4 to 5 mm., the inner diameter is from 1.5 to 2.5 mm., the thickness is from 1.0 to 1.5 mm. and the height is from 3 to 6 mm.

3. The molded catalyst of claim 1, wherein the catalyst is one prepared by using a compression type tabletting machine.

* * * * *